United States Patent [19]
Yamamoto et al.

[11] 4,297,356
[45] Oct. 27, 1981

[54] MEMORY ENHANCER CONTAINING 2-(7-INDENYLOXYMETHYL-MORPHOLINE

[75] Inventors: Minoru Yamamoto, Kanagawa; Shiro Tachikawa, Omiya; Hiroo Maeno, Shiki, all of Japan

[73] Assignee: Yamanouchi Pharmaceutical Co., Ltd., Tokyo, Japan

[21] Appl. No.: 181,068

[22] Filed: Aug. 25, 1980

[30] Foreign Application Priority Data

Mar. 5, 1980 [JP] Japan .................................. 55/26742

[51] Int. Cl.³ .............................................. A61K 27/00
[52] U.S. Cl. ................................................. 424/248.57
[58] Field of Search ................................... 424/248.57

[56] References Cited

U.S. PATENT DOCUMENTS 4,109,088  8/1978  Murakami et al. ............. 424/248.57

Primary Examiner—Stanley J. Friedman
Attorney, Agent, or Firm—Burgess, Ryan and Wayne

[57] ABSTRACT

A memory enhancer comprising a composition containing 2-(7-indenyloxymethyl)-morpholine or an acid addition salt thereof as the effective component.

4 Claims, No Drawings

MEMORY ENHANCER CONTAINING 2-(7-INDENYLOXYMETHYL-MORPHOLINE

This invention relates to a memory enhancer comprising a composition containing 2-(7-indenyloxymethyl) morpholine having the formula

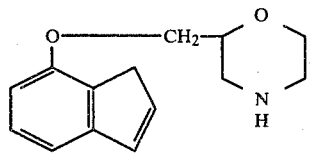

or an acid addition salt thereof as the effective component. Preferred examples of the acid addition salt are the hydrochloride, sulfate, maleate, etc.

2-(7-Indenyloxymethyl) morpholine used as the effective component in this invention is a compound previously reported as possessing an antidepressive activity (see, U.S. Pat. No. 4,109,088).

However, the results of a biological test have clearly shown that the compound unexpectedly possesses a strong memory and learning effect and is very useful as a memory enhancer for treatment in enhancing reduced mental faculty. Thus, pharmaceutical compositions containing, as an effective ingredient 2-(7-indenyloxymethyl)-morpholine can be used to treat senile dementia, presenile dementia, senility, amnesia, and dementia caused by head injury, brain operation, or disturbances of cerebral circulation.

The memory and learning effect in the case of using 2-(7-indenyloxymethyl) morpholine hydrochloride as an effective component of a pharmaceutical composition is as follows.

(1) Memory and learning effects tested using bright and dark compartments:

Male Wister rats of 6 weeks age were placed in a bright compartment of $12 \times 12 \times 25$ cm$^3$. The compartment was connected to a dark compartment of $38 \times 25 \times 25$ cm$^3$ through a hole of $5 \times 7$ cm$^2$. The rats were first held in the bright compartment for 30 seconds while closing the hole. When the hole was opened after 30 seconds, the animals moved to the dark compartment through the hole but since an electric current of 1.5 mA and 60 Hz was passing through the floor of the dark compartment, the animals received an electric shock at their feet. The rats receiving the electric shock returned to the bright compartment through the hole to escape such an electric shock. Ten minutes after the performance of the first test, the test was tried again and the time until the rats entered the dark compartment was measured. The test drug was administered intraperitoneally 30 minutes before testing. In addition, in contrast or as a control, a physiological sodium chloride solution only was administered. The test results were shown as the time (mean moved time) until the rats entered the dark compartment from the bright compartment observed in the second test and as the number of rats which did not enter the dark compartment during 20 minutes of the test.

In addition, the observation time in the test was 30 minutes and the results were evaluated by a Fisher's method. The results obtained are shown in Table I.

TABLE I

| | Memory and learning effects tested using bright and dark compartments | | | |
|---|---|---|---|---|
| Test drug | Dose[1] | No. of tests | No. of Rats[2] | Mean moved time (min.) |
| contrast (control) | — | 28 | 10 | 16.4 ± 2.0 |
| 2-(7-idenyl-oxymethyl)morpholine hydrochloride | 2.0 | 15 | 11* | 24.3 ± 1.8 |

[1]mg/kg by intraperitoneal administration.
[2]the number of rats which did not move from the bright compartment to the dark compartment over 20 minutes.
*This value showed the useful difference with a risk ratio of 5% as compared with the physiological sodium chloride solution administered groups.

As shown in Table I, by the administration of 2-(7-indenyloxymethyl)morpholine hydrochloride, the mean moved time was prolonged and the number of rats which did not move to the dark compartment over 20 minutes increased as compared with the case of the contrast (control) test. Hence, it is clear that the effective compound of the composition of this invention significantly increases the memory and learning effects tested using bright and dark compartments.

(2) Memory and learning effects tested using a maze:

A T-maze was used for the experiment. Each of male Wister rats of 6 weeks age was placed in each cage individually, food was provided freely to the rats during 5 days before the experiment and during the following 4 days of the experimental period, and an aqueous cane sugar solution was provided for 1 hour a day. The experiment was performed once a day.

The trial was started by releasing a rat in a starting point. The rat first began to explore and after a while, a rat reached a choice point, where the rat chose the left arm in which an aqueous cane sugar solution (intensifying factor) was placed or the right arm in which no such solution was placed. The rat finally reached the left arm of the maze, drank the aqueous cane sugar solution and then was returned from the T-maze apparatus to the individual cage.

The test was continued for 4 days and the starting time, running time and the number of choice errors were recorded. The test drug i.e., the effective component 2-(7-indenyloxymethyl)morpholine hydrochloride, was intraperitoneally administered 30 minutes before the test. In addition, a physiological sodium chloride solution only was administered to a contrast (control) group. The results are shown in Table II.

TABLE II

| Memory and learning effects tested using a maze: | | | | | | |
|---|---|---|---|---|---|---|
| 1. Starting time | | | | | | |
| | | No. of | Starting time (min) | | | |
| Test drug | Dose[1] | tests | 1 | 2 | 3 | 4 (day) |
| Contrast (control) | — | 30 | 0.7 ± 0.2 | 2.5 ± 0.5 | 3.7 ± 0.7 | 3.9 ± 0.5 |
| 2-(7-indenyloxymethyl)-morpholine hydrochloride | 2.0 | 30 | 0.6 ± 0.1 | 1.2 ± 0.3* | 1.9 ± 0.4* | 2.4 ± 0.4* |
| 2. Running time | | | | | | |

TABLE II-continued

| Memory and learning effects tested using a maze: | | | | | | |
|---|---|---|---|---|---|---|
| | | No. of | Running time (min) | | | |
| Test drug | Dose[1] | tests | 1 | 2 | 3 | 4 (day) |
| Contrast (control) | — | 30 | 4.4 ± 0.6 | 4.5 ± 0.5 | 4.4 ± 0.7 | 4.5 ± 0.7 |
| 2-(7-indenyloxymethyl)-morpholine hydrochloride | 2.0 | 30 | 4.7 ± 0.6 | 3.0 ± 0.5 | 2.3 ± 0.5* | 2.3 ± 0.5* |
| 3. Errors | | | | | | |
| | | No. of | Errors (times) | | | |
| Test drug | Dose[1] | tests | 1 | 2 | 3 | 4 (day) |
| Contrast (control) | — | 30 | 3.1 ± 0.4 | 1.9 ± 0.3 | 1.7 ± 0.3 | 1.5 ± 0.3 |
| 2-(7-indenyloxymethyl)-morpholine hydrochloride | 2.0 | 30 | 2.0 ± 0.3 | 1.0 ± 0.2** | 0.4 ± 0.2*** | 0.4 ± 0.2** |

[1]mg/kg by intraperitoneal administration.
*, , *The results show useful differences as compared with the contrast case (with a risk ratio of 5% (*), 1% (), or 0.1% (*)).

As shown in Table II, by the administration of 2-(7-indenyloxymethyl)morpholine hydrochloride, the starting time, running time, and the number of errors were markedly reduced as compared with the case of the contrast (control). Hence, it is clear that the effective component of the composition of this invention strongly increases the memory and learning effects tested using a maze.

(3) Acute toxicity:

After orally administering 2-(7-indenyloxymethyl) morpholine hydrochloride, $LD_{50}$ (mg/kg) was determined.

| $LD_{50}$ | 340 mg/kg (mouse) |
| | >1,000 mg/Kg (rat) |

The memory enhancer of this invention can be orally or parenterally administered in the form of a powder, granules, tablets, capsules, injections, suppositories, etc., by being mixed with suitable pharmaceutically acceptable carriers, excipients, diluents, etc. For example, the medicament is orally administered in an amount of 5–300 mg per day for an adult of average weight i.e., about 150 lbs., but that does may be, as a matter of course, changed according to age, weight, symptom, etc., of the patient.

| Prescription example. | |
|---|---|
| 2-(7-indenyloxymethyl)morpholine hydrochloride | 2.5 mg |
| Milk sugar | 72.5 mg |
| Starch | 25 mg |
| Talc | 4 mg |
| Magnesium stearate | 1 mg |

After mixing the above-described components and granulating the mixture, the granules were tableted according to a conventional procedure to provide a 125 mg tablet.

What is claimed is:

1. A method of enhancing memory in an adult requiring enhancement of said memory comprising administering to said adult on effective amount of a composition administering an effective amount of 2-(7-indenyloxymethyl)morpholine or an acid addition salt thereof and a pharmaceutically acceptable carrier therefor.

2. A method as claimed in claim 1 wherein the acid addition salt is the hydrochloride, sulfate or maleate.

3. A method as claimed in claim 1 wherein the acid addition salt is the hydrochloride.

4. A method as claimed in claim 1 wherein 2.5 to 300 mgs of the effective ingredient is administered.

* * * * *